United States Patent [19]

Mott

[11] Patent Number: 4,754,081

[45] Date of Patent: Jun. 28, 1988

[54] PROCESS FOR DEARYLATION OF ALKYLENEBISPHENOLS AND ALKYLTRISPHENOLS

[75] Inventor: Graham N. Mott, Corpus Christi, Tex.

[73] Assignee: Hoechst Celanese Corporation, Somerville, N.J.

[21] Appl. No.: 12,419

[22] Filed: Feb. 9, 1987

[51] Int. Cl.$^4$ .............................................. C07C 37/00
[52] U.S. Cl. .................................. 568/806; 568/449; 568/485; 568/486; 568/805
[58] Field of Search ........................ 568/805, 806, 495

[56] References Cited

U.S. PATENT DOCUMENTS 3,075,015  1/1963  Meyer .................................. 568/806
3,466,337  9/1969  Smith et al. ......................... 568/806

*Primary Examiner*—Werren B. Lone
*Attorney, Agent, or Firm*—Stuart D. Frenkel; Donald R. Cassady

[57] ABSTRACT

Alkylenebisphenols and alkyltrisphenols are dearylated under mild conditions of temperature and pressure in the absence of HF to obtain alkyl and/or alkenyl substitute or phenols and other related polymer products.

9 Claims, No Drawings

PROCESS FOR DEARYLATION OF ALKYLENEBISPHENOLS AND ALKYLTRISPHENOLS

BACKGROUND OF THE INVENTION

1. Field of the Invention

The present invention relates to the production of phenols and alkyl and/or alkenyl substituted phenols by the dearylation or cleavage of alkylenebisphenols and alkyltrisphenols. More specifically, the invention relates to the preparation of alkenyl phenol compounds such as p-isopropenylphenol and other related polymer products by carrying out the dearylation in the presence of hydrogen fluoride under mild conditions.

2. Description of the Prior Art

The dearylation of alkylenebisphenols such as bisphenol A, i.e., 2,2-bis(4-hydroxyphenyl) propane, has been carried out with acids or bases to yield p-isopropenylphenol and phenol. U.S. Pat. No. 3,466,337, for example, discloses the decomposition of bisphenol A by heating with an acid to form phenol and other products. The reaction is carried out at temperatures of 125° C. to 300° C. in the presence of an acid catalyst such as benzenesulfonic acid, toluenesulfonic acid, sodium hydrogen sulfate, phosphoric acid or benzenephosphonic acid. This method is also stated to be applicable to treatment of equivalent materials such as trisphenol, the product obtained by condensing isopropenylphenol with bisphenol. In U.S. Pat. No. 3,075,015, bisphenolic condensation products of phenols with aldehydes and ketones are split or dearylated under the influence of dilute aqueous solutions of alkali-metal hydroxides. European Pat. No. 0017852 discloses the cleavage of alkylenebisphenols and trisphenols to phenol and other by-products in the presence of hydrogen and a catalyst of nickel oxide, manganese oxide, and a metal oxide support. The reaction is carried out at temperatures of 250° C. to 400° C. While such acid or base-induced reactions may offer one or more advantages, all of these methods suffer the disadvantage of using harsh conditions of high temperatures and/or pressure. Accordingly, it is an object of this invention to provide an effective catalyst for the dearylation of alkylenebisphenols under mild conditions of temperature and pressure.

SUMMARY OF THE INVENTION

In accordance with the present invention, there is provided a method for dearylating alkylenebisphenols and alkyltrisphenols which comprises contacting the phenol with liquid hydrogen fluoride under mild conditions of temperature and pressure and for a period of time sufficient to effect dearylation and produce phenol and alkyl and/or alkenyl substituted phenols, and thereafter recovering a dearylated product.

DETAILED DESCRIPTION OF THE INVENTION

In a preferred embodiment of the invention, effective dearylation is achieved when the HF to alkylenebisphenol or alkyltrisphenol volume mole ratio is 20–50:1 at a temperature of about 30° C., under a pressure sufficient to maintain the HF in liquid phase and keep the desired quantity in the reaction zone. The liquid phase is essentially hydrogen fluoride in which the polyhydric phenol feed material is dissolved therein.

The HF to alkylenebisphenol or alkyltrisphenol volume mole ratio maintained in the reaction zone may broadly range from 1:1 to about 75:1, or more, but is generally in the range of 20:1 to 50:1.

The dearylation reaction is carried out by contacting the phenolic charge stock with the hydrogen fluoride under liquid phase conditions at temperatures ranging from 0° C. to 120° C., preferably within a range of 20° C. to 80° C., and most preferably at temperatures of 30° C. to 50° C. for a period of time ranging from about 15 minutes to 6 hours, preferably from 30 minutes to 4 hours. Quantitative yields have been obtained at ambient temperatures of 30° C. for a reaction period of 1 hour.

The HF is preferably in substantially anhydrous form but small amounts of water, up to about 2 weight percent, may be present. Minor amounts of boron trifluoride may also be used in conjunction with the hydrogen fluoride, if desired. The term "hydrogen fluoride" as used herein is thus intended to include any homogeneous catalyst whose essential active ingredient is hydrogen fluoride.

The pressure in the reaction zone is maintained sufficiently high to maintain a substantially liquid phase operation, e.g., from about 2.5 to 500 psig.

A wide variety of alkylenebisphenols and alkyltrisphenols may be dearylated according to the invention. Typically, the phenolic charge stocks can be represented by the general formula:

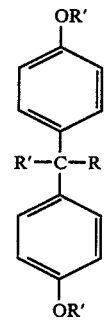

where R is hydrogen or an alkyl group of 1 to 9 carbon atoms and R' is hydrogen, an alkyl group of 1 to 9 carbon atoms, cycloalkyl, or an aryl group or functional derivative thereof, e.g., an esterified aryl group. The preferred phenolic charge stocks for purposes of dearylation include bis(4-hydroxyphenyl)alkanes and tris(4-hydroxyphenyl)alkanes such as 1,1-bis(4-hydroxyphenyl)methane, 1,1-bis(4-hydroxyphenyl)ethane, 2,2-bis(4-hydroxyphenyl)propane, 2,2-bis(4-hydroxyphenyl)butane, 2,2-bis(4-hydroxyphenyl)pentane, 3,3-bis(4-hydroxyphenyl)pentane, 1,1-bis(4-hydroxyphenyl) cyclohexane, 1,1-bis(4-hydroxyphenyl)-1-phenylethane, 1,1,1-tris(4-hydroxyphenyl)ethane, 4,4'-dihydroxy-trisphenyl-methane, 2,2-(4,4'-dihydroxydiphenyl)-2-phenyl-ethane, 4,4'-benzylidenedi(2-isopropylphenol) and the like. In a preferred embodiment the phenolic charge stocks are represented by the formula:

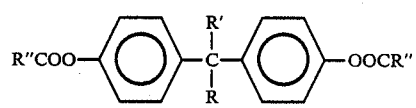

where R' is a hydrogen, alkyl, cycloalkyl, or an esterified aryl group, R is a hydrogen or an alkyl group having from 1 to 9 carbon atoms, and R" is an alkyl, cycloalkyl or an aryl group or functional derivative thereof.

The reaction mechanism for the dearylation of 1,1,1-tris(4-hydroxyphenyl)ethane (THPE) and bisphenol A may be illustrated as follows:

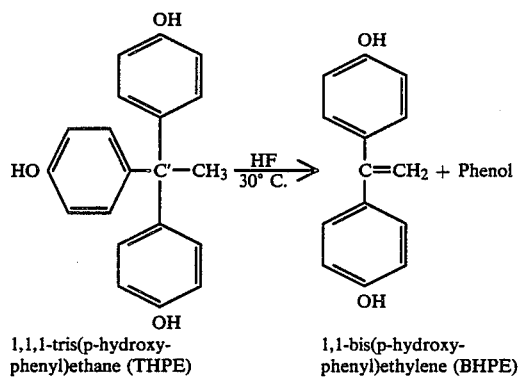

1,1,1-tris(p-hydroxyphenyl)ethane (THPE)

1,1-bis(p-hydroxyphenyl)ethylene (BHPE)

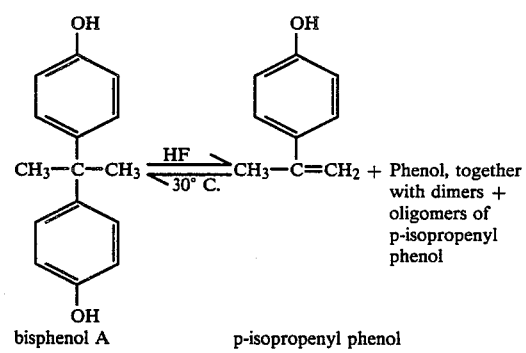

bisphenol A p-isopropenyl phenol

To overcome problems with reaction equilibria, the same reaction may also be carried out in the presence of a protective or blocking agent, e.g., acetic anhydride, propionic anhydride, or other known organic equivalent such as acetic acid, acetyl halides, etc., to yield p-isopropenylphenylacetate monomer and 4-HAP (4-hydroxyacetophenone), the latter by concommitant Fries rearrangement of by-product phenyl acetate. 4-HAP does not react with the vinyl products under these reaction conditions. In the presence of acetic anhydride, reaction I will yield BHPE and stable monomeric products such as 4,4'-bis-acetoxyphenylethylene and 4-hydroxy, 4'-acetoxyphenylethylene. The protective or blocking agent may be any monovalent organo group for R' and R" which does not preclude ester formation during dearylation. Examples include alkyl, alkenyl, aryl, aralkyl and cycloalkyl.

Esterified alkylidenebisphenols such as bisphenol A diacetate can be dearylated quantitatively as follows:

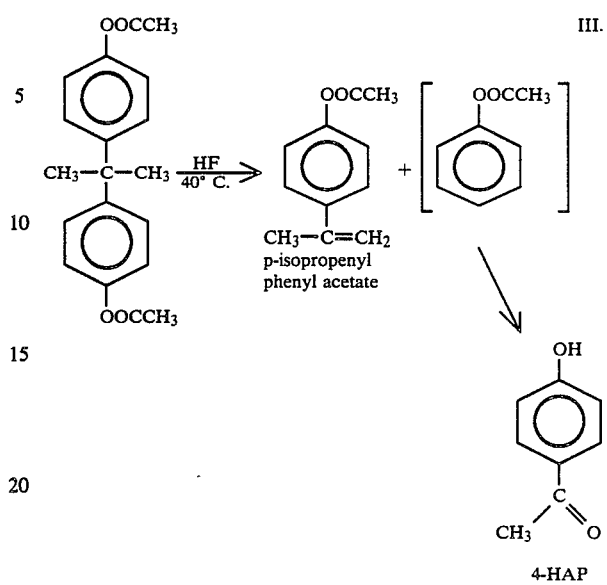

p-isopropenyl phenyl acetate

4-HAP

The following examples illustrate the best mode now contemplated for carrying out the invention.

EXAMPLE 1

This example illustrates the preparation of 1,1-bis(p-hydroxyphenyl)ethylene (BHPE) and phenol by dearylation of 1,1,1-tris(p-hydroxyphenyl)ethane (THPE) under liquid phase conditions in the presence of hydrogen fluoride as the catalyst.

To a 300 ml autoclave (Hastelloy C) were added 30.6 grams (0.1 mole) 1,1,1-tris(p-hydroxyphenyl)ethane. The autoclave was cooled to $-10°$ C. and evacuated to 175 Torr whereupon 100 grams (5 moles) of substantially anhydrous hydrogen fluoride was transferred from a cylinder to the autoclave at a temperature of 30° C. and pressure of 50 mm Hg. After the transfer of hydrogen fluoride was completed, the internal temperature and pressure of the autoclave were maintained at 30° C. and a pressure of 5 psig using nitrogen. The contents of the autoclave were stirred for 90 minutes at 30° C. and at the end of the reaction, excess hydrogen fluoride was vented through a caustic (KOH) scrubber and the contents of the autoclave flushed with nitrogen. The resulting organic phase was dissolved in ethyl acetate and the ethyl acetate phase recovered from the aqueous phase. The ethyl acetate phase was evaporated. 12 Grams (57%) of bishydroxyphenylethylene (BHPE) crystallized and was recovered by filtration. By-product phenol can be removed from the oily residue by steam stripping and additional BHPE recovered. No other organic products or THPE were observed in the product mixture.

EXAMPLE 2

This example illustrates the liquid phase preparation of p-isopropenyl phenol by the dearylation of bisphenol A using hydrogen fluoride as the catalyst.

The procedure of Example 1 was repeated using 22.8 grams (0.10 mole) bisphenol A and 100 grams (5 moles) of hydrogen fluoride. The reaction was carried out for 90 minutes at 30° C., after which a mixture containing 8.8 gms of phenol, 7.9 gms of bisphenol A, and 4.1 gms of p-isopropenylphenol (monomer, dimers and oligomers) was recovered.

The same reaction may also be carried out at 40° C. for 3 hours using 22.8 grams (0.10 moles) bisphenol A and 150 grams (7.5 moles) of hydrogen fluoride to yield a mixture containing 6.7 gms of phenol, 11.8 gms of bisphenol A and 5.6 gms of p-isopropenylphenol (monomer, dimers and oligomers).

Following the same procedure, at 30° C. for 3 hours using 22.8 grams (0.10 mole) of bisphenol A and 100 grams (5 moles) of hydrogen fluoride, a mixture containing 5.1 gms of phenol, 7.7 gms of bisphenol A and 8.5 gms of p-isopropenylphenol (monomer, dimers and oligomers) was obtained.

Following the same procedure, at 40° C. for 17 hours using 22.8 gms (0.10 mole) of bisphenol A and 150 gms (7.5 moles) of hydrogen fluoride yielded a mixture containing 7.1 gms of phenol, 12.5 gms of bisphenol A and 5.7 gms of p-isopropenylphenol (monomer, dimers and oligomers).

EXAMPLE 3

This example illustrates the liquid phase preparation of 1,1-bis(p-hydroxyphenyl)ethylene (BHPE) by the dearylation of 1,1,1-tris(p-hydroxyphenyl)ethane (THPE) using hydrogen fluoride and acetic anhydride.

The procedure of Example 1 was followed using 30.6 grams (0.1 mol) THPE, 45.9 grams (0.45 mole) acetic anhydride, and 100 grams (5 moles) hydrogen fluoride. The reaction was carried out for about 2 hours at 70° C. after which a mixture containing 4-hydroxyacetophenone (4-HAP), 2-hydroxyacetophenone (2-HAP), bishydroxyphenylethylene (BHPE), 4-hydroxy, 4'-acetoxyphenylethylene, and 4,4'-bisacetoxyphenylethylene was recovered. No phenol or THPE was detected in the product mix.

The same amount of reactants of Example 3 were also reacted to produce the same products at a temperature of 30° C. for 90 minutes.

EXAMPLE 4

This example illustrates the liquid phase preparation of p-isopropenylphenylacetate by the dearylation of bisphenol A diacetate using hydrogen fluoride as the catalyst.

The procedure of Example 1 was followed using 772 grams (2.5 moles) of bisphenol A diacetate and 3200 grams (80 moles) of hydrogen fluoride. The reaction was carried out for 4 hours at 40° C. after which a mixture containing 4-hydroxyacetophenone (4-HAP), 2-hydroxyacetophenone (2-HAP), p-isopropenylphenylacetate, p-isopropenylphenol (monomer, dimers and oligomers) was recovered. A minor amount of phenol (1%) but no bisphenol A diacetate was detected in the product mix.

What is claimed is:

1. In a process for dearylating an alkylenebisphenol or alkyltrisphenol, the improvement which comprises contacting said alkylenebisphenol or alkyltrisphenol with hydrogen fluoride under liquid phase conditions and for a period of time sufficient to dearylate said phenol and produce phenol and alkyl and/or alkenyl substituted phenols, said phenol having the formula:

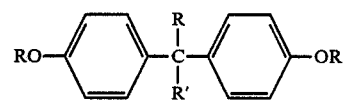

wherein R is hydrogen or an alkyl group of 1 to 9 carbon atoms and R' is hydrogen, an alkyl group of 1 to 9 carbon atoms, cycloalkyl, an aryl group, or functional derivatives thereof.

2. The process of claim 1 wherein the temperature is in the range of 0° to 120° C. and the pressure is in the range of 2.5 to 500 psig.

3. The process of claim 2 wherein said contacting is carried out for less than 8 hours.

4. The process of claim 1, 2 or 3 wherein said phenol is a bis(4-hydroxyphenyl)alkane.

5. The process of claim 1, 2 or 3 wherein said phenol is a tris(4-hydroxyphenyl)alkane.

6. The process of claim 4 wherein said phenol is 2,2-bis(4-hydroxyphenyl) propane.

7. The process of claim 5 wherein said phenol is 1,1,1-tris(4-hydroxyphenyl)ethane.

8. The process of claim 6 or 7 wherein the dearylation is carried out in the presence of a monovalent organo protective or end blocking group.

9. The process of claim 1 wherein the alkylenebisphenol is represented by the formula:

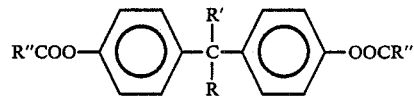

where R' is a hydrogen, alkyl, cycloalkyl, or an esterified aryl group, R is a hydrogen or an alkyl group having from 1 to 9 carbon atoms and R" is an alkyl, cycloalkyl, an aryl group, or functional derivative thereof.

* * * * *